United States Patent
Au et al.

(10) Patent No.: US 9,682,028 B2
(45) Date of Patent: *Jun. 20, 2017

(54) PERSONAL CARE PHOTOPROTECTIVE COMPOSITIONS WITH TRICYCLODECANE AMIDES

(71) Applicant: Conopco, Inc., Englewood Cliffs, NJ (US)

(72) Inventors: Van Au, Oxford, CT (US); Bijan Harichian, Brookfield, CT (US); Ian Stuart Cloudsdale, Chapel Hill, NC (US); John Steven Bajor, Cheshire, CT (US); John Kenneth Dickson, Jr., Apex, NC (US)

(73) Assignee: Conopco, Inc., Englewood Cliffs, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/771,273

(22) PCT Filed: Mar. 10, 2014

(86) PCT No.: PCT/EP2014/054606
§ 371 (c)(1),
(2) Date: Aug. 28, 2015

(87) PCT Pub. No.: WO2014/139965
PCT Pub. Date: Sep. 18, 2014

(65) Prior Publication Data
US 2016/0045419 A1   Feb. 18, 2016

Related U.S. Application Data

(60) Provisional application No. 61/778,816, filed on Mar. 13, 2013.

(51) Int. Cl.
| | | |
|---|---|---|
| A61K 8/49 | (2006.01) | |
| A61Q 19/02 | (2006.01) | |
| A61Q 17/04 | (2006.01) | |
| A61K 8/42 | (2006.01) | |

(52) U.S. Cl.
CPC ............ *A61K 8/4926* (2013.01); *A61K 8/42* (2013.01); *A61K 8/49* (2013.01); *A61K 8/4906* (2013.01); *A61K 8/4913* (2013.01); *A61K 8/4973* (2013.01); *A61Q 17/04* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 4,956,481 A | 9/1990 | Gillaspey | |
| 4,985,403 A | 1/1991 | Narula | |
| 5,135,747 A | 8/1992 | Faryniarz | |
| 5,212,203 A | 5/1993 | Shroot | |
| 5,212,303 A | 5/1993 | Shroot | |
| 5,833,999 A | 11/1998 | Trinh | |
| 5,849,310 A | 12/1998 | Trinh | |
| 6,086,903 A | 7/2000 | Trinh | |
| 6,100,233 A | 8/2000 | Sivik | |
| 6,399,045 B1 | 6/2002 | Morgan | |
| 6,576,228 B1 | 6/2003 | Crookham | |
| 8,053,431 B2 | 11/2011 | Kilburn | |
| 8,173,108 B2 | 5/2012 | Misso | |
| 2003/0003119 A1 | 1/2003 | Bekele | |
| 2004/0228814 A1 | 11/2004 | Candau | |
| 2006/0024337 A1 | 2/2006 | Simonnet | |
| 2006/0057083 A1 | 3/2006 | Mathonneau | |
| 2006/0062746 A1* | 3/2006 | Brillouet | A61K 8/645 424/59 |
| 2006/0166856 A1 | 7/2006 | Petrat | |
| 2011/0104082 A1 | 5/2011 | Polonka | |
| 2011/0104087 A1 | 5/2011 | Polonka et al. | |
| 2012/0004206 A1 | 1/2012 | Pliushchev | |

FOREIGN PATENT DOCUMENTS

| | | |
|---|---|---|
| DE | 10337579 | 4/2004 |
| DE | 10337579 | 4/2014 |
| EP | 0199636 | 2/1989 |
| EP | 1010685 | 6/2000 |
| ES | 2296463 | 4/2008 |
| ES | 2296463 | 2/2009 |
| WO | WO9918919 | 6/1999 |
| WO | WO03075878 | 9/2003 |
| WO | WO2004089415 | 10/2004 |
| WO | WO2004089416 A2 | 10/2004 |
| WO | WO2004089470 A3 | 10/2004 |
| WO | WO2005019162 | 3/2005 |

(Continued)

OTHER PUBLICATIONS

Search Report PCTEP2014054604 dated Jun. 11, 2014.
Search Report PCTEP2014054606 dated Jun. 11, 2014.
Written Opinion 1 in PCTEP2014054604 dated Jun. 11, 2014.
Written Opinion 1 in PCTEP2014054606 dated Jun. 11, 2014.
Akhrem et al., "Alkanes and cycloalkanes in the one-pot synthesis of amides", Mendeleev Communications, 2007, vol. 17, pp. 279-280.
Akhrem et al., "The first one-pot amidation of alkanes and cycloalkanes", Tetrahedron Letters, Jan. 10, 2008, vol. 49, pp. 1399-1404.

(Continued)

*Primary Examiner* — Ernst V Arnold
*Assistant Examiner* — Kyung Sook Chang
(74) *Attorney, Agent, or Firm* — Rimma Mitelman

(57) ABSTRACT

A personal care photoprotective composition is provided having a UV-A and UV-B sunscreen in conjunction with a tricyclodecane amide. The tricyclodecane amide functions to boost UV-A, UV-B and SPF performance when the personal care composition is applied to skin or hair of the human body.

14 Claims, No Drawings

(56) References Cited

FOREIGN PATENT DOCUMENTS

| WO | WO2006119283 A2 | 11/2006 |
|----|-----------------|---------|
| WO | WO2008054144    | 5/2008  |
| WO | WO2011054704    | 6/2011  |

OTHER PUBLICATIONS

Kasemura et al., "Miticidal Activity of Monoterpenyl Carboxypyrrolidinamides and Piperidinamides", Journal of Oleo Science, 2003, vol. 52, No. 1, pp. 41-46.
Kontonassios et al., "3-(Dialkylamino)methyladamantane-1-carboxylic Acids", Notes, Apr. 29, 1968, vol. 12, pp. 170-172.
Egan et al., Raoult's law and vapor pressure measurement, Journal of Chemical Education, May 1, 1976, vol. 53, No. 5, p. 303.
Schafer et al., "Facile synthesis of Sterically Hindered and Electron-Deficient Secondary Amides from Isocyanates", Angew. Chem. Int. Edition, Sep. 3, 2012, vol. 51, No. 36, pp. 9173-9175; XP055120011.
Schuster et al., "The Discovery of New 11B-Hydroxysteroid Dehydrogenase Type 1 Inhibitors by Common Feature Pharmacophore Modeling and Virtual Screening", Journal of Medical Chem, 2006, vol. 49, pp. 3454-3466, 49.
Search Report in PCTEP2014054587 dated Oct. 14, 2014.
Terao et al., "11B-Hydroxysteroid Dehydrogenase-1 Is a Novel Regulator of Skin Homeostasis and a Candidate Target for Promoting Tissue Repair", PLos One, Sep. 2011, vol. 6 Iss 9, pp. 1-11.
Tiganescu et al., "Localization, Age-and Site-Dependent Expression, and Regulation of 11B-Hydroxysteroid Dehydrogenase Type 1 in Skin", Journal of Invesitgative Dermatology, 2011, vol. 131, pp. 30-36.
Hermanowski-Vosatka et al., "11B-HSD1 inhibition ameliorates metabolic syndrome and prevents progression of atherosclerosis in mice", Journal of Experimental Medicine, Aug. 15, 2005, vol. 202, No. 4, pp. 517-527, vol. 202 No. 4.
Webster et al., "Discovery and biological evaluation of adamantyl amide 11B-HSD1 inhibitors", Bioorganic & Medicinal Chemistry Letters, 2007, vol. 17, pp. 2838-2843, 17.
Written Opinion 2 in PCTEP2014054604 dated Feb. 10, 2015.
Written Opinion 2 in PCTEP2014054606 dated Feb. 10, 2015.
Written Opinion in PCTEP2014054587 dated Oct. 14, 2014.

* cited by examiner

PERSONAL CARE PHOTOPROTECTIVE COMPOSITIONS WITH TRICYCLODECANE AMIDES

FIELD OF THE INVENTION

The invention relates to personal care compositions with improved UV-A, UV-B, and SPF protection.

BACKGROUND OF THE INVENTION

Solar radiation includes about 5% ultraviolet (UV) radiation, wavelength of which is between 200 nm and 400 nm. It is further classified into three regions: from 320 to 400 nm (UV-A), 290 to 320 nm (UV-B) and from 200 to 290 nm (UV-C). A large part of UV-C radiation is absorbed by the ozone layer. Scientific studies have indicated that exposure to UV-A and UV-B radiation for short period causes reddening of the skin and localized irritation, whereas continued and prolonged exposure can lead to sunburn, melanoma and formation of wrinkles and age spots. It is also reported that UV radiation causes significant damage to hair. Therefore, it is desirable to protect the skin and other keratinous substrates of the human body from the harmful effects of both UV-A and UV-B radiation, in addition to increasing the SPF protection.

Various cosmetic preparations have been reported for preventing and/or protecting the skin from harmful effects of ultraviolet radiation. Numerous organic sunscreen agents capable of absorbing UV-A rays are reported in the field of cosmetics amongst which a particularly useful sunscreen is t-butylmethoxydibenzoylmethane (a.k.a avobenzone, also sold as Parsol 1789). Many UV-B sunscreens are also known and approved for safe use in personal care compositions for protection from UV-B radiation. Many cosmetic manufacturers prefer to include both UV-A and UV-B sunscreens in photoprotective compositions so as to provide protection over the entire range of UV radiation.

Thus, cosmetic manufacturers aim to provide consumers with products having better and better sun protection. One of the ways of achieving this is to incorporate higher and higher levels of UV-A and UV-B sunscreens. One disadvantage of this approach is the high cost associated with incorporation of high levels of sunscreens which are expensive. Further, there are safety and regulatory limitations on the upper limit of incorporation of these sunscreens. Finally, sensory properties are also altered on incorporation of sunscreens, particularly when the amounts of sunscreens are increased. Many topical compositions have a unique sensory feel that consumers come to recognize and love and associate with the particular brand or composition. As the knowledge of the harmful effects of UV exposure developed, it became desirable to improve UV-A and UV-B protection substantially, without increasing levels of UV-A and UV-B protection. This is not trivial, particularly for non-solid personal care formulations, since sunscreens tend to have high impact on viscosity, drying behavior, and other tactile and sensory characteristics of the formulation. It is critical to preserve the sensory profile of the composition while achieving a substantial UV-A and UV-B boost. If the feel of the formulation is altered, consumer loyalty may quickly change The present inventors have unexpectedly determined that by virtue of incorporating tricyclodecane amides along with UV-A and UV-B sunscreens, a significant boost in UV-A and UV-B protection, and in SPF, can be achieved. The present inventors further unexpectedly determined that tricyclodecane amides suppress sebum production, which is advantageous in photoprotection compositions which tend to contain relatively high amounts of oil—excess sebum exacerbates oily feel of such compositions.

Tricyclodecane derivatives, and in some cases tricyclodecane amides, have been described. See for instance Kilburn et al., U.S. Pat. No. 8,053,431B2; WO2004/089415A2 (Novo Nordisk NS); WO2004/089416A2 (Novo Nordisk NS); Narula et al., U.S. Pat. No. 4,985,403; Mathonneau, US 2006057083; WO06/119283 (Hunton & Williams LLP); WO08/054144 (Amorepacific Corporation); Other amides have been used for boosting UV protection—see e.g. US2011/0104087 (Unilever), but they did not achieve the improvement for both the UV-A and UV-B, only UV-A.

SUMMARY OF THE INVENTION

The present invention includes a personal care composition comprising:
a. from 1 to 20%, by weight of the composition, of an organic UV-B sunscreen;
b. from 1 to 10%, by weight of the composition of an organic UV-A sunscreen;
c. from 0.001 to 30% of a tricyclodecane amide; and
d. a cosmetically acceptable carrier.

The invention also includes methods of caring for skin or hair, by applying to the skin or hair the compositions according to the present invention. The invention also includes methods of improving UV-A, UV-B and SPF protection. The invention further includes methods of sebum suppression.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

The compositions of the invention are preferably non-solid. "Non-solid" as used herein with respect to the composition means that the composition has a measurable viscosity (measurable for instance with a Brookfield Viscometer DV-I+(20 RPM, RV6, 30 Seconds, 20° C.) in the range of from 1 Pas to 500 Pas, preferably from 2 Pas to 100 Pas, more preferably from 3 Pas to 50 Pas.

"Personal Care Composition" as used herein, is meant to include a composition for topical application to sun-exposed areas of the skin and/or hair of humans. Such a composition may be generally classified as leave-on or rinse off, and includes any product applied to a human body for also improving appearance, cleansing, odor control or general aesthetics. The composition of the present invention can be in the form of a liquid, lotion, cream, foam, scrub, gel, or toner, or applied with an implement or via a face mask, pad or patch. Non-limiting examples of such sunscreen compositions include leave-on skin lotions, creams, antiperspirants, deodorants, foundations, mascara, sunless tanners and sunscreen lotions and wash-off shampoos, conditioners, shower gels. The composition of the present invention is preferably a leave-on composition, because such compositions are the most challenging in terms of boosting UV-A/UV-B/SPF yet without increasing oil amounts.

"Skin" as used herein is meant to include skin on the face and body (e.g., neck, chest, back, arms, underarms, hands, legs, buttocks and scalp) and especially to the sun exposed parts thereof. The composition of the invention is also of relevance to applications on any other keratinous substrates of the human body other than skin e.g. hair where products may be formulated with specific aim of improving photoprotection.

Sunscreen

The composition of the invention comprises from 0.1 to 10%, preferably from 0.5 to 7%, most preferably from 1 to 5% of UVA sunscreen. Preferred UVA sunscreen is t-butyl-methoxydibenzoylmethane (a.k.a. avobenzone), 2-methyl-dibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. Other suitable UV-A sunscreens include but are not limited to Bisdisulizole disodium (Neo Heliopan AP), Diethylamino hydroxybenzoyl hexyl benzoate (Uvinul A Plus), Ecamsule (Mexoryl SX), Methyl anthranilate.

The composition of the invention also comprises 0.1 to 20%, preferably from 1 to 10%, more preferably from 0.5 to 7%, most preferably from 2 to 6%, of an oil soluble or water-soluble UV-B organic sunscreen. The oil soluble UV-B organic sunscreen is preferably selected from the class of cinnamic acid, salicylic acid, diphenyl acrylic acid or derivatives thereof. A few of the preferred oil soluble UV-B sunscreens which are commercially available and useful for inclusion in the composition of the invention are Octisalate™ (octyl salicylate), Homosalate™ (3,3,5-trimethylcyclohexyl 2-hydroxybenzoate), Neo Heliopan™ (a range of organic UV filters including ethylhexyl methoxycinnamate (Neo Heliopan AV) and ethylhexyl salicylate (Neo Heliopan OS)), Octocrylene™ (2-ethylhexyl 2-cyano-3,3-diphenyl-2-propenoate) or Parsol MCX™ (known as 2-ethylhexyl-4-methoxycinnamate or octylmethoxycinnamate). According to a particularly preferred aspect of the invention the oil soluble UVB sunscreen is 2-ethylhexyl 4-methoxycinnamate. According to another particularly preferred aspect of the invention the oil soluble UVB sunscreen is 2-ethylhexyl 2-cyano-3,3-diphenyl-2-propenoate. Water-soluble UV-B sunscreens include but are not limited to: Phenylbezimidazole Sulfonic Acid (also known as ensulizole); salicylates, PABA.

Especially preferred oil soluble UVB sunscreen is selected from 2-ethylhexyl 2-cyano-3,3-diphenyl-2-propenoate which is commercially available as Octocrylene™, Parsol MCX also known as octyl methoxy cinnamate, and mixtures thereof.

A particularly preferred combination of UV-A and UV-B sunscreens is avobenzone (a.k.a. Parsol 1789) and octylmethoxycinnamate (a.k.a. Parsol MCX).

Additional suitable sunscreens can be used available from BASF corporation: Uvinul T-150 (Ethylhexyl triazone), Uvinul A Plus (Diethylamino hydroxybenzoyl hexyl benzoate), Tinosorb S (bis-ethylhexyloxyphenol methoxyphenyl triazine), Tinosorb M (methylene bis-benzotriazolyl tetramethylbutylphenol).

The present inventors seek to improve UV-A and UV-B protection with use of relatively small amounts of sunscreens, e.g. total organic sunscreens of less than 25%, preferably less than 15%, and optimally less than 10% by weight of the composition.

Tricyclodecane Amides

There generally is no limitation with respect to the tricyclodecane amide that may be used in this invention other than that the same is suitable for use in compositions used by consumers. Often, however, the tricyclodecane amide suitable for use in this invention is represented by at least one compound having Formula I or Formula II. Tricyclodecane amides of Formula I are preferred.

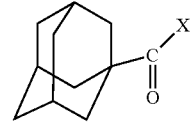

Formula I

Where X is selected from:

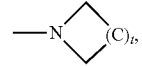

Xa

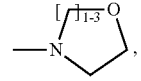

Xb

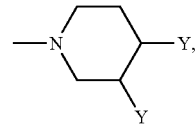

Xc

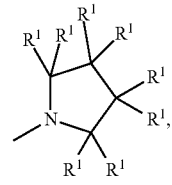

Xd

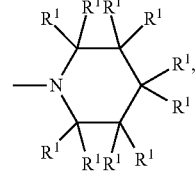

Xe

-continued

Xf 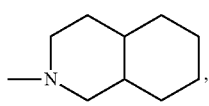

Xg 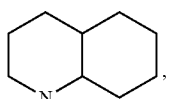

Xh 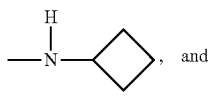, and

Xi 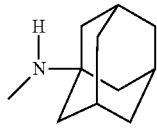

further wherein
t is an integer from 1 to 8; Y is hydrogen,

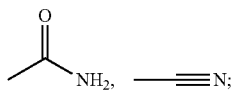

or a halogen
where each $R^1$ is independently a hydrogen or a $C_{1\ to\ 4}$ alkyl.

Preferably, X is selected from groups Xd, Xe, Xf, Xg and, and more preferably Xd and Xe, ideally X is selected from groups Xe and Xd, wherein $R^1$ is hydrogen on all but one carbon and is mono- or di-substituted on that single carbon with methyl or ethyl groups.

Preferred Formula I compounds, wherein X is group Xa, Xb, Xc, Xd, Xe, Xf, Xg, Xh, Xi are:

Methanone, (morphonyl)tricyclo[3.3.1.1$^{3,7}$]dec-1-yl- (C1)
Methanone, (piperidinyl)tricyclo[3.3.1.1$^{3,7}$]dec-1-yl- (C2)
Methanone, (pyrrolidinyl)tricyclo[3.3.1.1$^{3,7}$]dec-1-yl- (C3)
Methanone, (azetidinyl)tricyclo[3.3.1.1$^{3,7}$]dec-1-yl- (C4)
Methanone, (hexahydroazepinyl)tricyclo[3.3.1.1$^{3,7}$]dec-1-yl- (C5)
Methanone, (4-cyano-piperidinyl)tricyclo[3.3.1.1$^{3,7}$]dec-1-yl- (C6)
Methanone, (4-amido-piperidinyl)tricyclo[3.3.1.1$^{3,7}$]dec-1-yl- (C7)
Methanone, (Tricyclo[3.3.1.1$^{3,7}$]decanyl)-N-tricyclo[3.3.1.1$^{3,7}$]dec-1-yl- (C8))
Methanone, (decahydroisoquinolinyl)tricyclo[3.3.1.1$^{3,7}$]dec-1-yl- (C9))
Methanone, (decahydroquinolinyl)tricyclo[3.3.1.1$^{3,7}$]dec-1-yl- (C10))
Methanone, (3,3-dimethyl-1-piperidinyl)tricyclo[3.3.1.1$^{3,7}$]dec-1-yl- (C11))
Methanone, (2-methyl-1-piperidinyl)tricyclo[3.3.1.1$^{3,7}$]dec-1-yl- (C12))
Methanone, (4-methyl-1-piperidinyl)tricyclo[3.3.1.1$^{3,7}$]dec-1-yl-(C13))
Methanone, (3-methyl-1-piperidinyl)tricyclo[3.3.1.1$^{3,7}$]dec-1-yl-(C14))
Methanone, (3,5-dimethyl-1-piperidinyl)tricyclo[3.3.1.1$^{3,7}$]dec-1-yl-(C15))
Methanone, (4-methyl-4-ethyl-piperidinyl)tricyclo[3.3.1.1$^{3,7}$]dec-1-yl- (C16))
Methanone, (3,3-diethyl-1-pyrrolidinyl)tricyclo[3.3.1.1$^{3,7}$]dec-1-yl- (C17)

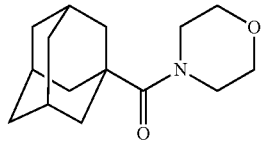 (C1)

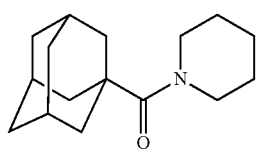 (C2)

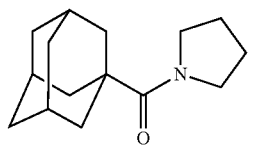 (C3)

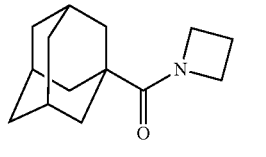 (C4)

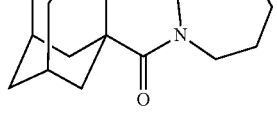 (C5)

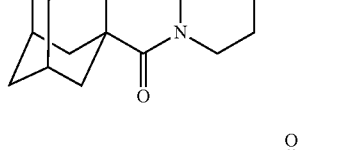 (C6)

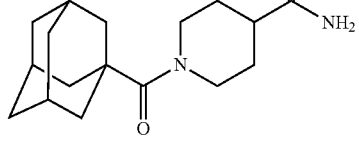 (C7)

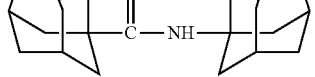 (C8)

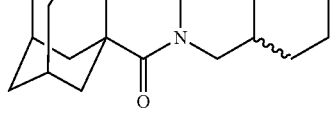 (C9)

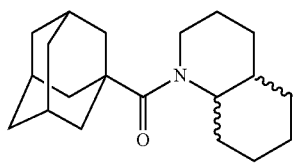
(C10)

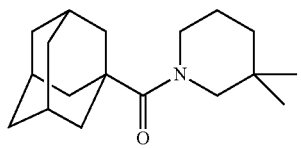
(C11)

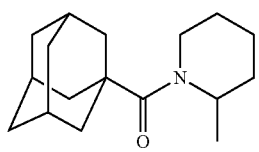
(C12)

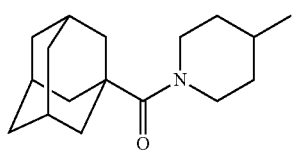
(C13)

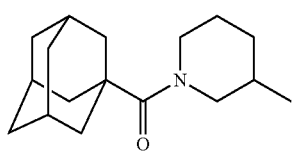
(C14)

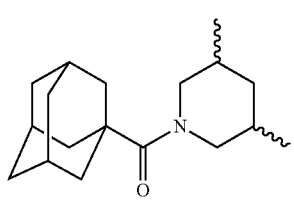
(C15)

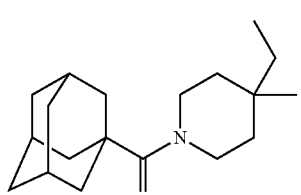
(C16)

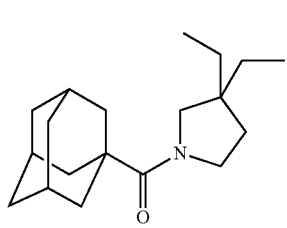
(C17)

More preferred compounds are compounds C9 through C17, and most preferred compounds are C11 through C17.

Tricyclodecane amides of Formula II have the following general structure:

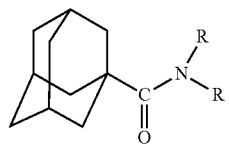
Formula II wherein each R is independently hydrogen, methyl, ethyl or a $C_3$ to $C_{18}$, preferably $C_3$ to $C_{10}$, linear or branched alkyl, cycloalkyl or cycloheteroalkyl group with the proviso that both R groups are not simultaneously hydrogen; and (iii) a cosmetically acceptable carrier.

Preferably R is a linear or branched alkyl with substitution on tertiary nitrogen.

Example of formula II preferred structures are:

Methanone, (N,N-diisopropyl)tricyclo[3.3.1.1$^{3,7}$]dec-1-yl- (C18))

Methanone, (3,3-dimethylbutylaminyl)tricyclo[3.3.1.1$^{3,7}$]dec-1-yl- (C19))

Methanone, (2,2-dimethylpropylaminyl)tricyclo[3.3.1.1$^{3,7}$]dec-1-yl- (C20))

Methanone, (1,1-dimethyl-3,3-dimethylbutylaminyl)tricyclo[3.3.1.1$^{3,7}$]dec-1-yl-(C21))

Methanone, (1,3-dimethyl-butylaminyl)tricyclo[3.3.1.1$^{3,7}$]dec-1-yl- (C22)

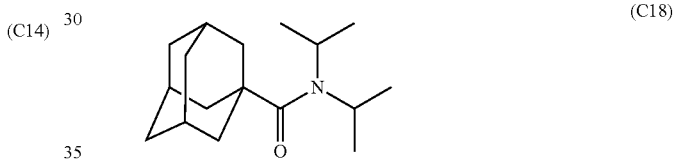
(C18)

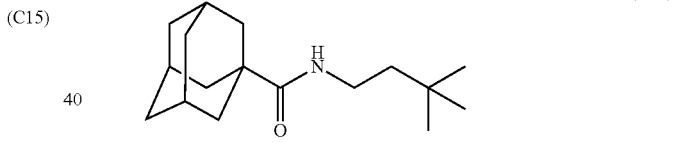
(C19)

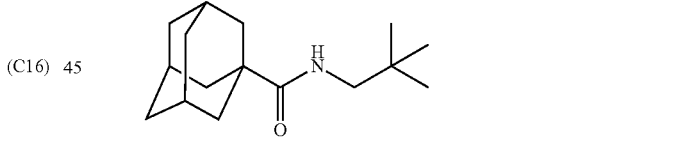
(C20)

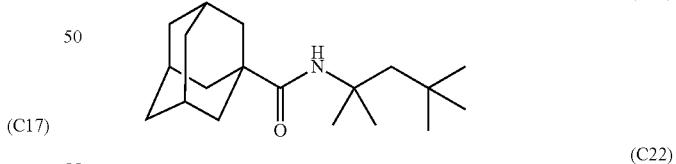
(C21)

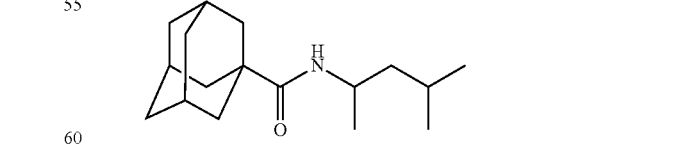
(C22)

Wherein compounds C19, C20, C21 and C22 are more preferred, and compounds C21 and C22 most preferred.

The amount of tricyclodecane amide is generally in the range of from 0.0001 to 20%, preferably from 0.001 to 10%, more preferably from 0.01% to 5%, most preferably from 0.5% to 10%.

Other tricyclodecane amides and other tricyclodecane derivatives may be included in the inventive composition, in addition to the tricyclodecane amides described herein.

Carrier

Compositions of this invention also include a cosmetically acceptable carrier.

Amounts of the carrier may range from 1 to 99.9%, preferably from 70 to 95%, optimally from 80 to 90% by weight of the composition. Among the useful carriers are water, emollients, fatty acids, fatty alcohols, thickeners and combinations thereof. The carrier may be aqueous, anhydrous or an emulsion. Preferably the compositions are aqueous, especially water and oil emulsions of the water-in-oil or oil-in-water type or multiple emulsions of the water-in-oil-in-water or oil-in-water-in-oil variety. Water when present may be in amounts ranging from 5 to 95%, preferably from 20 to 70%, optimally from 35 to 60% by weight.

Emollient materials may serve as cosmetically acceptable carriers. These may be in the form of silicone oils, natural or synthetic esters, hydrocarbons, alcohols and fatty acids. Amounts of the emollients may range anywhere from 0.1 to 95%, preferably between 1 and 50% by weight of the composition.

Silicone oils may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 5 to 6, silicon atoms.

Nonvolatile silicone oils useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from $5 \times 10^{-6}$ to $0.1$ $m^2/s$ at 25° C. Among the preferred nonvolatile emollients useful in the present compositions are the polydimethyl siloxanes having viscosities from $1 \times 10^{-5}$ to $4 \times 10^{-4}$ $m^2/s$ at 25° C.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Among the ester emollients are:
a) Alkyl esters of saturated fatty acids having 10 to 24 carbon atoms. Examples thereof include behenyl neopentanoate, isononyl isonanonoate, isopropyl myristate and octyl stearate.
b) Ether-esters such as fatty acid esters of ethoxylated saturated fatty alcohols.
c) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.
d) Wax esters such as beeswax, spermaceti wax and tribehenin wax.
e) Sugar ester of fatty acids such as sucrose polybehenate and sucrose polycottonseedate.

Natural ester emollients principally are based upon mono-, di- and tri-glycerides.

Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from 0.1 to 20% by weight of the compositions.

Hydrocarbons which are suitable cosmetically acceptable carriers include petrolatum, mineral oil, $C_{11}$-$C_{13}$ isoparaffins, polybutenes and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids and mixtures thereof.

Fatty alcohols having from 10 to 30 carbon atoms are another useful category of cosmetically acceptable carrier. Illustrative of this category are stearyl alcohol, lauryl alcohol, myristyl alcohol, oleyl alcohol and cetyl alcohol and mixtures thereof.

Thickeners can be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides (e.g. Sepigel 305®), acryloylmethylpropane sulfonic acid/salt polymers and copolymers (e.g. Aristoflex HMB® and AVC®), cellulosic derivatives and natural gums. Among useful cellulosic derivatives are sodium carboxymethylcellulose, hydroxypropyl methocellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Inorganics may also be utilized as thickeners, particularly clays such as bentonites and hectorites, fumed silicas, talc, calcium carbonate and silicates such as magnesium aluminum silicate (Veegum®). Amounts of the thickener may range from 0.0001 to 10%, usually from 0.001 to 1%, optimally from 0.01 to 0.5% by weight of the composition.

Preferred are emollients that can be used, especially for products intended to be applied to the face, to improve sensory properties and are chosen from the group of oils that do not form stiff gels with 12HSA; these include polypropylene glycol-14 butyl ether otherwise known as Tegosoft PBE, or PPG15 stearyl ether such as Tegosoft E, other oils such as esters, specifically, isopropyl myristate, isopropyl palmitate, other oils could include castor oils and derivatives thereof.

Humectants of the polyhydric alcohol-type can be employed as cosmetically acceptable carriers. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of humectant may range anywhere from 0.5 to 50%, preferably between 1 and 15% by weight of the composition.

Skin moisturizers, e.g. hyaluronic acid and/or its precursor N-acetyl glucosamine may be included. N-acetyl glucosamine may be found in shark cartilage or shitake mushrooms and are available commercially from Maypro Industries, Inc (New York). Other preferred moisturizing agents include hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from 0.2 to 30%, and preferably from 0.5 to 20%, optimally from 1% to 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-dihydroxyethyl urea; N,N'-di-hydroxypropyl urea; N,N,N'-trihydroxyethyl urea; tetra(hydroxymethyl) urea; tetra(hydroxyethyl) urea; tetra(hydroxypropyl urea; N-methyl, N'-hydroxyethyl urea; N-ethyl-N'-hydroxyethyl urea; N-hydroxypropyl-N'-hydroxyethyl urea and N,N'-dimethyl-N-hydroxyethyl urea. Where the term hydroypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea that may be used in the topical composition of this invention range from 0.01 to 20%, and preferably, from 0.5 to 15%, and most preferably, from 2 to 10% based on total weight of the composition and including all ranges subsumed therein.

When ammonium salt and substituted urea are used, in a most especially preferred embodiment at least from 0.01 to 25%, and preferably, from 0.2 to 20%, and most preferably, from 1 to 15% humectant, like glycerine, is used, based on total weight of the topical composition and including all ranges subsumed therein.

Inorganic sunblocks may be preferably used in the present invention. These include, for example, zinc oxide, iron oxide, silica, such as fumed silica, or titanium dioxide. The total amount of sun block that is preferably incorporated in the composition according to the invention is from 0.1 to 10% by weight of the composition.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, caprylyl glycol, $C_{1-6}$ parabens (especially, methyl paraben and/or propyl paraben), imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition, including all ranges subsumed therein. An especially preferred combination is octocrylene and caprylyl glycol, since caprylyl glycol has been disclosed to enhance UVA and UVB protection.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

Form of the Composition

The compositions of the present invention are preferably non-solid. The compositions of the invention are preferably leave-on compositions. The compositions of the present invention are intended to be applied to remain on the skin. These leave-on compositions are to be distinguished from compositions which are applied to the skin and subsequently removed either by washing, rinsing, wiping, or the like either after or during the application of the product. Surfactants typically used for rinse-off compositions have physicochemical properties giving them the ability to generate foam/lather in-use with ease of rinse; they can consist of mixtures of anionic, cationic, amphoteric, and nonionic. Surfactants used in leave-on compositions on the other hand are not required to have such properties. Rather, as leave-on compositions are not intended to be rinsed-off they need to be non-irritating and therefore it would be necessary to minimize the total level of surfactant and the total level of anionic surfactant in leave-on compositions. The total level of anionic surfactant in the inventive compositions is preferably no more than 10%, more preferably below 8%, most preferably at most 5%, optimally at most 3%.

The compositions of the present invention are typically in the form of emulsions, which may be oil-in-water, or water-in-oil; preferably the compositions are oil-in-water emulsions. The most preferred format are vanishing cream base and creams based on an oil-in-water emulsion. Vanishing cream base is one which comprises 5 to 40% fatty acid and 0.1 to 20% soap. In such creams, the fatty acid is preferably substantially a mixture of stearic acid and palmitic acid and the soap is preferably the potassium salt of the fatty acid mixture, although other counterions and mixtures thereof can be used. The fatty acid in vanishing cream base is often prepared using hystric acid which is substantially (generally about 90 to 95%) a mixture of stearic acid and palmitic acid.

A typical hystric acid comprises about 52-55% palmitic acid and 45-48% stearic acid of the total palmitic-stearic mixture. Thus, inclusion of hystric acid and its soap to prepare the vanishing cream base is within the scope of the present invention. It is particularly preferred that the composition comprises higher than 7%, preferably higher than 10%, more preferably higher than 12% fatty acid.

A typical vanishing cream base is structured by a crystalline network and is sensitive to the addition of various ingredients. The invention is particularly advantageous for vanishing cream base because the addition of the tricyclodecane amides does not significantly impact this crystalline network structure thereby preserving the sensory profile during application.

Rheology Modifier

A rheology modifier may be included and is selected from the group consisting of silica such as fumed silica or hydrophilic silicas and clays such as magnesium aluminum silicate, betonites, hectorite, laponite, and mixtures thereof. A rheology modifier is employed in an amount of from 0.01 to 2%, preferably from 0.05 to 1%.

Skin Benefit Ingredients

The inventive composition preferably includes an additional skin lightening compound, to obtain optimum skin lightening performance at an optimum cost. Illustrative substances are placental extract, lactic acid, niacinamide, arbutin, kojic acid, ferulic acid, hydroquinone, resorcinol and derivatives including 4-substituted resorcinols and combinations thereof. More preferably, such additional skin lightening compound is a tyrosinase inhibitor, to complement the melanogenesis inhibition activity of the substituted monoamines, most preferably a compound selected from the group consisting of kojic acid, hydroquinone and 4-substituted resorcinol. Also, dicarboxylic acids represented by the formula HOOC—(CxHy)-COOH where x=4 to 20 and y=6 to 40 such as azelaic acid, sebacic acid, oxalic acid, succinic acid, fumaric acid, octadecenedioic acid or their salts or a mixture thereof, most preferably fumaric acid or salt thereof, especially di-sodium salt. It has been found that combination of 12HSA with fumaric acid or salts thereof are particularly preferred, especially for skin lightening formulations. Amounts of these agents may range from 0.1 to 10%, preferably from 0.5 to 2% by weight of the composition. It is preferred that the skin lightening coactive according to the invention is vitamin B3 or a derivative thereof and is selected from the group consisting of niacinamide, nicotinic acid esters, non-vasodilating esters of nicotinic acid, nicotinyl amino acids, nicotinyl alcohol esters of carboxylic acids, nicotinic acid N-oxide, niacinamide N-oxide and mixtures thereof.

Another preferred ingredient of the inventive compositions is a retinoid. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and U.S. Pat. No. Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. The retinoid is preferably substantially pure, more preferably essentially pure. The compositions of this invention may contain a safe and effective amount of the retinoid, such that the resultant composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from 0.005% to 2%, more preferably 0.01% to 2%, retinoid. Retinol is preferably used in an amount of from 0.01% to 0.15%; retinol esters are preferably used in an amount of from 0.01% to 2% (e.g., 1%); retinoic acids are preferably used in an amount of from 0.01% to 0.25%; tocopheryl-retinoate, adapalene, and tazarotene are preferably used in an amount of from 0.01% to 2%.

A variety of herbal extracts may optionally be included in compositions of this invention. Illustrative are pomegranate, white birch (*Betula Alba*), green tea, chamomile, licorice and extract combinations thereof. The extracts may either be water soluble or water-insoluble carried in a solvent which respectively is hydrophilic or hydrophobic. Water and ethanol are the preferred extract solvents.

Also included may be such materials as resveratrol, alpha-lipoic acid, ellagic acid, kinetin, retinoxytrimethylsilane (available from Clariant Corp. under the Silcare 1 M-75 trademark), dehydroepiandrosterone (DHEA) and combinations thereof. Ceramides (including Ceramide 1, Ceramide 3, Ceramide 3B, Ceramide 6 and Ceramide 7) as well as pseudoceramides may also be utilized for many compositions of the present invention but may also be excluded. Amounts of these materials may range from 0.000001 to 10%, preferably from 0.0001 to 1% by weight of the composition.

Colorants, opacifiers and abrasives may also be included in compositions of the present invention. Each of these substances may range from 0.05 to 5%, preferably between 0.1 and 3% by weight of the composition.

Method of Using Compositions

The composition according to the invention is intended primarily as a product for topical application to human skin, especially as an agent for conditioning and smoothening the skin, composition for protecting from solar radiation, and preventing or reducing the appearance of wrinkled or aged skin, or age spots, or lightening of the skin.

In use, a small quantity of the composition, for example from 1 to 5 ml, is applied to exposed area of the skin, from a suitable container or applicator and, if necessary, it is then spread over and/or rubbed into the skin using the hand or fingers or a suitable device.

While the above summarizes the present invention, it will become apparent to those skilled in the art that modifications, variations and alterations may be made without deviating from the scope and spirit of the present invention as described and claimed herein. The invention will now be further illustrated in the following non-limiting examples.

EXAMPLES

Experimental Methods

All reagents and solvents were obtained from commercial sources (Sigma-Aldrich, EMD Chemicals) and used as supplied unless otherwise indicated. Parallel reactions and parallel solvent removal were performed using a Buchi Syncore reactor (Buchi Corporation, New Castle, Del.). Reaction monitoring was performed using thin layer chromatography (TLC). TLC was performed using silica gel 60 F254 plates (EMD Chemicals) and visualizing by UV (254 nm), 4% phosphomolybdic acid (PMA) in ethanol (EtOH), 4% ninhydrin in ethanol and/or using an iodine chamber. Flash chromatography (FC) was performed using a Biotage SP4 system (Biotage LLC, Charlottesville, Va.). High performance liquid chromatography (HPLC) was performed using a Waters 2695 Separations Module equipped with a Waters 2996 Photodiode Array Detector and operated with Empower Pro software (Waters Corp.). Separations were carried out at 1 ml/min on a Restek Pinnacle DB C18 column (5 μm, 4.6×150 mm) maintained at 30° C. Examples for HPLC were prepared by dissolving 1 mg of example in 1 ml mobile phase A:B (1:1) and injecting 5 μL onto the column. The mobile phase consisted of A=0.1% trifluoroacetic acid (TFA) in water and B=0.1% TFA in acetonitrile (ACN) operated using gradient elution from 95:5 A:B to 5:95 A:B (gradient, 25 min) followed by 100% B (isocratic, 5 min). Gas Chromatography (GC) was performed using an Agilent 7890A Gas Chromatograph equipped with an Agilent DB-5HT (15 m×0.32 mm; 0.1μ) column and an FID detector heated at 325° C. Examples were prepared at 25 ppm concentrations in acetone and the injection volume was 1 μL. The air, helium and hydrogen flows were maintained at 400, 25 and 30 ml/min and the separation gradient consisted of 100° C. (isothermal, 1 min), 15° C./min up to 250° C., 250° C. (isothermal, 4 min), 25° C./min up to 300° C., and 300° C. (isothermal, 3 min). Liquid chromatography/mass spectrometry (LC-MS) was performed using a Finnigan Mat LCQ Mass Spectrometer via direct infusion of examples (50 ppm) in methanol and the total ion count monitored using electrospray ionization in the (+) mode (ESI+). 1H and 13C Nuclear magnetic resonance (NMR) spectroscopy was performed using a Eft-60 NMR Spectrometer (Anasazi instruments, Inc.) and processed using Win-Nuts software (Acorn NMR, Inc.). Melting points were determined using a Meltemp apparatus (Laboratory Devices). Purity was determined by HPLC-UV/Vis and/or GC. All compounds were unequivocally confirmed by LC-MS and/or $^1$H NMR. DCM=Dichloromethane; DIPEA=N, N-Diisopropylethylamine; RT=room temperature; MTBE=Methyl tert-Butyl ether; TFA=Trifluroacetic acid; ACN=acetonitrile; IPA=isopropyl alcohol; FC=flash chromatography.

Examples 1 through 28 as shown demonstrate the synthesis of tricyclodecane amides suitable for use in this invention.

General Procedure

Tricyclo[3.3.1.1$^{3,7}$]decane-1-carbonyl chloride was stirred under nitrogen atmosphere in Dichloromethane and the solution was cooled to 0° C. in an ice bath. A solution of a chosen amine was slowly added to the solution of Tricyclo[3.3.1.1$^{3,7}$]decane-1-carbonyl chloride. Upon completion of addition the reaction mixture was warmed up to room temperature and stirred under N$_2$ overnight. Work up: water was added to the reaction mixture and was extracted with dichlromethane, washed with 0.1 N HCl, water, sat. NaHCO$_3$ and sat. NaCl solution, dried over Sodium sulfate and evaporated on the rotovap. The solid was purified by a silica gel filtration (silica gel bed, used 15% ethyl acetate in hexane). The filtrate was evaporated on the rotovap, to give pure white crystalline corresponding amides.

Example 1

Synthesis of Methanone, (3,3-dimethyl-1-piperidinyl)tricyclo[3.3.1.1$^{3,7}$]dec-1-yl (Compound C11)

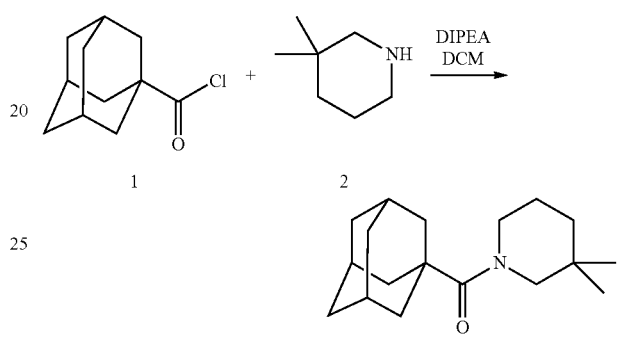

DIPEA (144 μL, 0.8 mmol) was added to a solution of Tricyclo[3.3.1.1$^{3,7}$]decane-1-carbonyl chloride (1) (150 mg, 0.8 mmol) and 3,3-dimethylpiperidine (2) (85 mg, 0.8 mmol) in DCM (2 ml) and the solution stirred at room temperature for 1 hour. At this time, TLC [15:85 EA:hexane, 20 μL aliquot into MTBE:1 N HCl (400 μL:400 μL)] showed the formation of a single product. The reaction mixture was allowed to stir for and additional 16 hours. The solution was diluted with CHCl$_3$ (10 ml), washed with 1N HCl (10 ml), saturated NaHCO$_3$ (10 ml), dried (Na$_2$SO$_4$), filtered and the solvents removed to give crude product as a colorless oil (160 mg). The product was further purified by FC on silica gel using 15:85 EA:hexane to give the desired product as a white solid.

Example 2

Synthesis of Methanone, (decahydroisoquinolinyl)tricyclo[3.3.1.1$^{3,7}$]dec-1-yl- (C9)

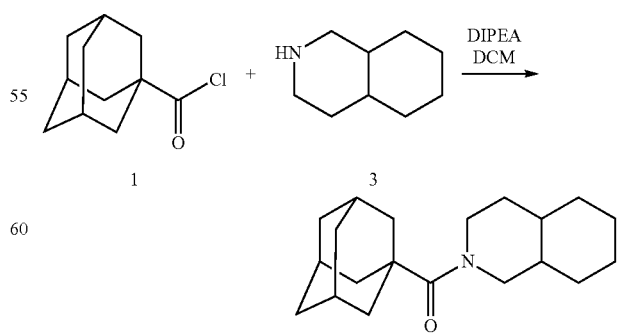

DIPEA (1.93 ml, 11.1 mmol) was added to a solution of Tricyclo[3.3.1.1$^{3,7}$]decane-1-carbonyl chloride (1) (2 g, 10.1 mmol) and decahydroisoquinoline (3) (1.59 ml, 11.1 mmol) in DCM (20 ml) and the solution stirred at room temperature for 4 hours. At this time, TLC [15:85 EA:hexane, 20 μL aliquot into MTBE:1 N HCl (400 μL:400 μL)] showed the formation of a single product. The solution was washed with 0.1 N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 3

Synthesis of Methanone, (4,4-dimethyl-1-piperidinyl)tricyclo[3.3.1.1$^{3,7}$]dec-1-yl

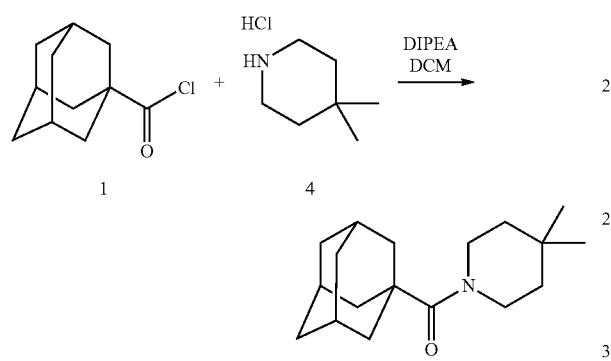

DIPEA (1.93 ml, 11.1 mmol) was added to a solution of Tricyclo[3.3.1.1$^{3,7}$]decane-1-carbonyl chloride (1) (1 g, 5.5 mmol) and 4,4-dimethylpiperidine hydrochloride (4) (828 mg, 5.5 mmol) in DCM (10 ml) and the solution stirred at room temperature for 4 hours. At this time, TLC [15:85 EA:hexane, 20 μL aliquot into MTBE:1 N HCl (400 μL:400 μL)] showed the formation of a single chemical. The solution was washed with 0.1N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a crystalline white solid.

Example 4

Synthesis of Methanone, (cyclopentylaminyl)tricyclo[3.3.1.1$^{3,7}$]dec-1-yl

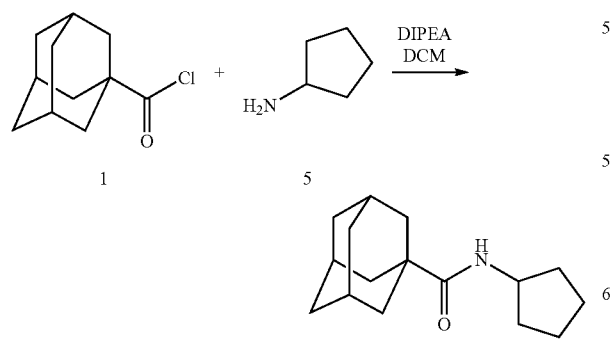

DIPEA (1.93 ml, 11.1 mmol) was added to a solution of Tricyclo[3.3.1.1$^{3,7}$]decane-1-carbonyl chloride (1) (2 g, 10.1 mmol) and cyclopentylamine (5) (1.09 ml, 11.1 mmol) in DCM (20 ml) and the solution stirred at room temperature for 4 hours. At this time, TLC [15:85 EA:hexane, 20 μL aliquot into MTBE:1 N HCl (400 μL:400 μL)] showed the formation of a single product. The solution was washed with 0.1 N HCl (30 ml), saturated NaHCO$_3$ (30 ml), dried (Na$_2$SO$_4$), filtered and the solvents removed to give crude product which was further purified via crystallization from 15% EA in hexanes to give the desired product as a white solid.

Example 5

Synthesis of Methanone, (4-methyl-1-piperidinyl)tricyclo[3.3.1.1$^{3,7}$]dec-1-yl (Compound C13)

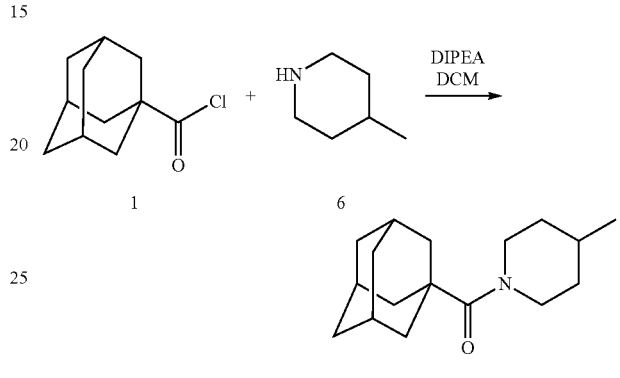

DIPEA (1.93 ml, 11.1 mmol) was added to a solution of Tricyclo[3.3.1.1$^{3,7}$]decane-1-carbonyl chloride (1) (1 g, 5.5 mmol) and 4-methylpiperidine (6) (1.27 ml, 11.1 mmol) in DCM (20 ml) and the solution stirred at room temperature for 4 hours. At this time, TLC [15:85 EA:hexane, 20 μL aliquot into MTBE:1 N HCl (400 μL:400 μL)] showed the formation of a single product. The solution was washed with 0.1N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 6

Synthesis of Methanone, (3-methyl-1-piperidinyl)tricyclo[3.3.1.1$^{3,7}$]dec-1-yl (Compound C14)

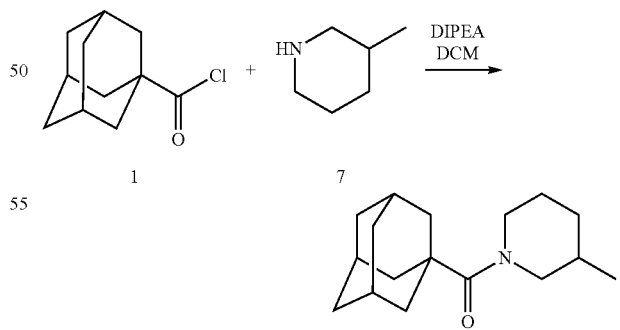

DIPEA (1.93 ml, 11.1 mmol) was added to a solution of Tricyclo[3.3.1.1$^{3,7}$]decane-1-carbonyl chloride (1) (1 g, 5.5 mmol) and 3-methylpiperidine (7) (1.31 ml, 11.1 mmol) in DCM (20 ml) and the solution stirred at room temperature for 4 hours. At this time, TLC[15:85 EA:hexane, 20 μL aliquot into MTBE:1 N HCl (400 μL:400 μL)] showed the formation of a single product and some SM remaining. The solution was washed with 0.1N HCl (30 ml), saturated NaHCO₃ (30 ml), dried (Na₂SO₄), filtered and the solvents removed to give crude product which was further purified by FC on silica gel using 15:85 EA:hexane to give the desired product as a white solid.

Example 7

Synthesis of Methanone, (4-amido-piperidinyl)tricyclo[3.3.1.1³,⁷]dec-1-yl- (Compound C7)

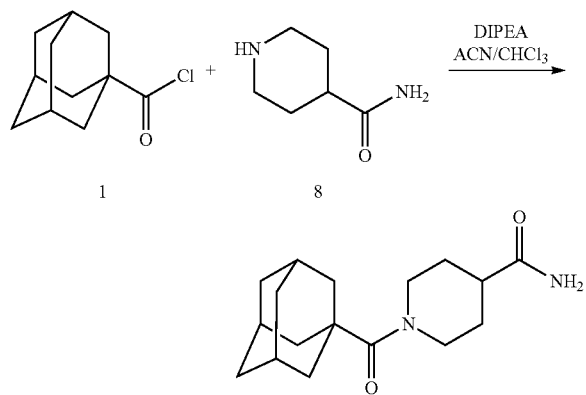

4-Piperidinecarboxamide (8) (71 mg, 0.6 mmol) was dissolved in ACN:CHCl₃ (3 ml, 1:1) solution by gentle warming. DIPEA (96 µL, 0.6 mmol) was added, followed by Tricyclo[3.3.1.1³,⁷]decane-1-carbonyl chloride (1) (100 mg, 0.5 mmol) and the solution stirred at room temperature for 20 hours. At this time, TLC [7% MeOH in CHCl₃, 20 µL aliquot into MTBE:1 N HCl (400 µL:400 µL)] showed the formation of a single product. The solution was diluted with 15% IPA in CHCl₃ (8 ml), washed with 0.1N HCl (8 ml), saturated NaHCO₃ (8 ml), dried (Na₂SO₄), filtered and the solvents removed to give crude product which was further purified by FC on silica gel using 7% MeOH in CHCl₃ to give product as a white solid.

Example 8

Synthesis of Methanone, (3-cyano-piperidinyl)tricyclo[3.3.1.1³,⁷]dec-1-yl-

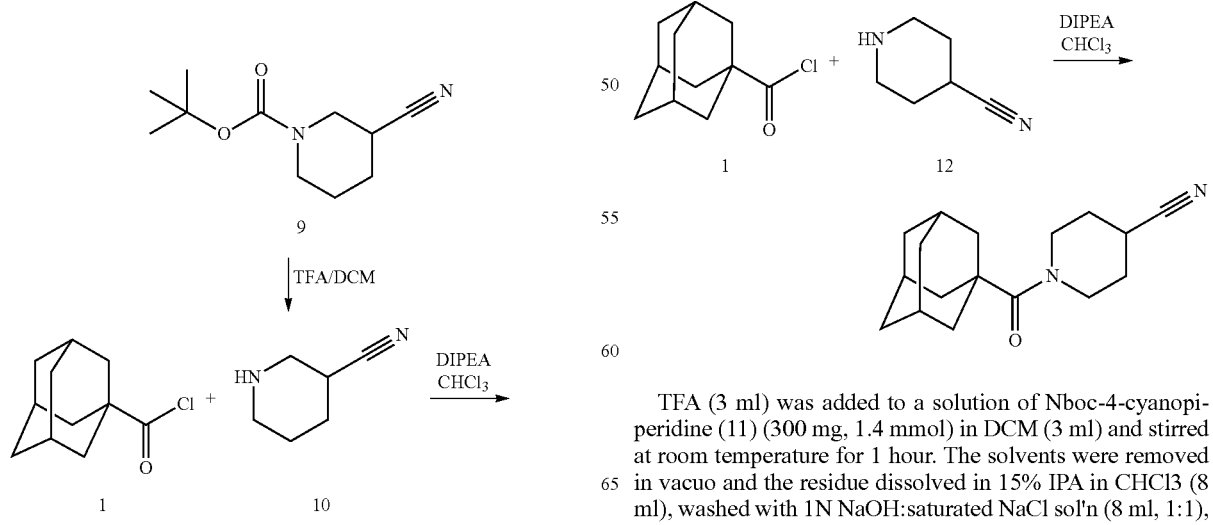

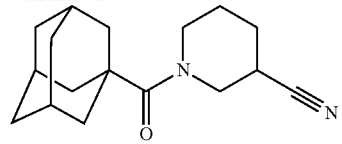

TFA (3 ml) was added to a solution of Nboc-3-cyanopiperidine (9) (300 mg, 1.4 mmol) in DCM (3 ml) and stirred at room temperature for 1 hour. The solvents were removed in vacuo and the residue dissolved in 15% IPA in CHCl3 (8 ml), washed with 1N NaOH:saturated NaCl sol'n (8 ml, 1:1), dried (Na₂SO₄), filtered and the solvents removed to give 3-cyanopiperidine (10) (141 mg, 90% yield) which was used crude for the next step. Tricyclo[3.3.1.1³,⁷]decane-1-carbonyl chloride (1) (100 mg, 0.5 mmol) was added to a solution of 3-cyanopiperidine (10) (61 mg, 0.6 mmol) and DIPEA (96 µL, 0.6 mmol) in CHCl₃ (1 ml) and the solution stirred at room temperature for 16 hours. At this time, TLC [40:60 EA:hexane, 20 µL aliquot into MTBE:1 N HCl (400 µL:400 µL)] showed the formation of a major product. The solution was diluted with CHCl₃ (8 ml), washed with 0.1N HCl (8 ml), saturated NaHCO₃ (8 ml), dried (Na₂SO₄), filtered and the solvents removed to give crude product which was further purified by FC on silica gel using 40:60 EA:hexane to give product as a white solid.

Example 9

Synthesis of Methanone, (4-cyano-piperidinyl)tricyclo[3.3.1.1³,⁷]dec-1-yl (Compound C6)

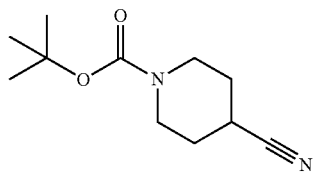

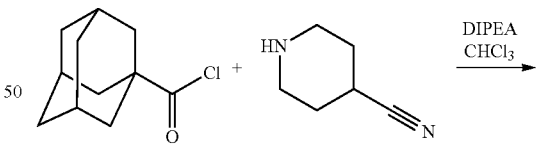

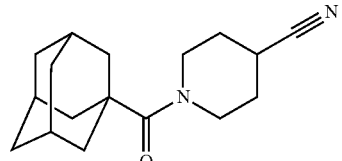

TFA (3 ml) was added to a solution of Nboc-4-cyanopiperidine (11) (300 mg, 1.4 mmol) in DCM (3 ml) and stirred at room temperature for 1 hour. The solvents were removed in vacuo and the residue dissolved in 15% IPA in CHCl3 (8 ml), washed with 1N NaOH:saturated NaCl sol'n (8 ml, 1:1), dried (Na₂SO₄), filtered and the solvents removed to give 4-cyanopiperidine (12) (141 mg, 90% yield) which was used crude for the next step. Tricyclo[3.3.1.1³,⁷]decane-1-carbonyl chloride (1) (230 mg, 1.2 mmol) was added to a solution of 4-cyanopiperidine (12) (140 mg, 1.3 mmol) and DIPEA (222 μL, 1.3 mmol) in CHCl₃ (2 ml) and the solution stirred at room temperature for 16 hours. At this time, TLC [40:60 EA:hexane, 20 μL aliquot into MTBE:1 N HCl (400 μL:400 μL)] showed the formation of a major product. The solution was diluted with CHCl₃ (8 ml), washed with 0.1N HCl (8 ml), saturated NaHCO₃ (8 ml), dried (Na₂SO₄), filtered and the solvents removed to give crude product which was further purified by FC on silica gel using 40:60 EA:hexane to give product as a white solid.

Example 10

Synthesis of Methanone, (1,1-dimethyl-3,3-dimethylbutylaminyl)tricyclo[3.3.1.1³,⁷]dec-1-yl- (Compound C21)

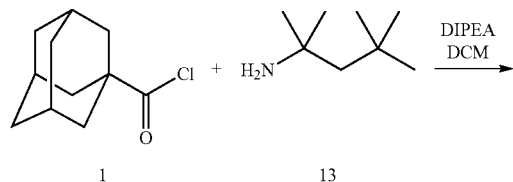

Tricyclo[3.3.1.1³,⁷]decane-1-carbonyl chloride (1) (300 mg, 1.5 mmol) was stirred under nitrogen atmosphere in DCM (3 mL) and the solution was cooled to 0° C. in an ice bath. DIPEA (300 μL, 1.7 mmol) and 1,1-dimethyl-3,3-dimethylbutylamine (13) (271 μL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified by FC on silica gel using 15% EA in hexane to give product as a white solid.

Example 11

Synthesis of Methanone, (3,3-dimethylbutylaminyl)tricyclo[3.3.1.1³,⁷]dec-1-yl- (Compound C19)

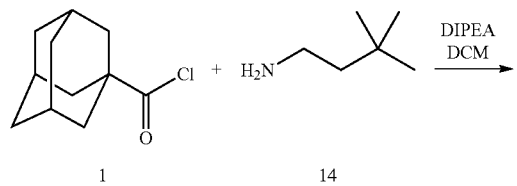

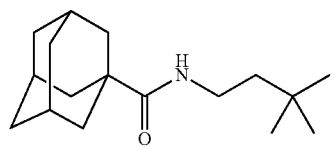

Tricyclo[3.3.1.1³,⁷]decane-1-carbonyl chloride (1) (300 mg, 1.5 mmol) was stirred under nitrogen atmosphere in DCM (3 mL) and the solution to 0° C. in an ice bath. DIPEA (300 μL, 1.7 mmol) and 3,3-dimethylbutylamine (14) (228 μL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified by FC on silica gel using 15% EA in hexane to give product as a white solid.

Example 12

Synthesis of Methanone, (decahydroquinolinyl)tricyclo[3.3.1.1³,⁷]dec-1-yl- (Compound C10)

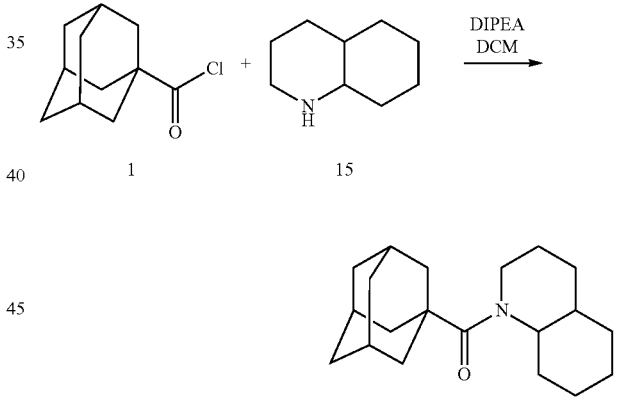

Tricyclo[3.3.1.1³,⁷]decane-1-carbonyl chloride (1) (40.0 g, 0.200 moles) was stirred under nitrogen atmosphere in DCM (340 mL, 1.2 M) and the solution cooled to 0° C. in an ice bath. DIPEA (27.3 g, 18.44 mL, 0.210 moles) and decahydroquinoline (15) (28.35 g, 30.28 mL, 0.210 moles) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified on silica gel (filtration through a 3" bed of silica gel) using 15:85 EA:hexane to give product as a white crystalline solid.

Example 13

Synthesis of Methanone, (TRANS-decahydroquinolinyl)tricyclo[3.3.1.1^{3,7}]dec-1-yl-

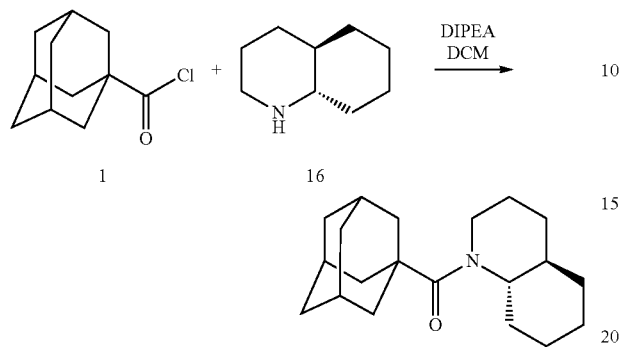

Tricyclo[3.3.1.1^{3,7}]decane-1-carbonyl chloride (1) (200 mg, 1 mmoles) was added to a solution of trans-decahydroquinoline (16) (154 mg, 1.1 mmoles) and DIPEA (193 µL, 1.1 mmoles) in CHCl$_3$ (2 ml) and the solution stirred at room temperature for 16 hours. The reaction mixture was diluted with CHCl$_3$ (8 ml) and washed sequentially with 0.1 N HCl, saturated NaHCO$_3$, dried (Na$_2$SO$_4$), filtered and the solvents removed to give crude product which was purified by FC on silica gel using 7% EA in hexane to give product as a white solid.

Example 14

Methanone, (azetidinyl)tricyclo[3.3.1.1^{3,7}]dec-1-yl- (Compound C4)

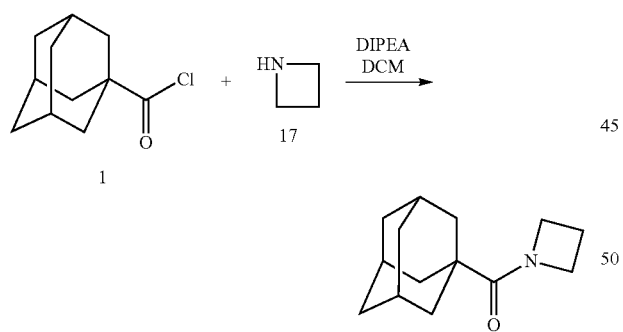

Tricyclo[3.3.1.1^{3,7}]decane-1-carbonyl chloride (1) (300 mg, 1.6 mmol) was stirred under nitrogen atmosphere in DCM (3 mL) and the solution cooled to 0° C. in an ice bath. DIPEA (540 µL, 3.1 mmol) and azetidine hydrochloride (17) (148 mg, 1.6 mmol) were mixed and added to the Tricyclo[3.3.1.13,7]decane-1-carbonyl chloride solution slowly. The reaction mixture was allowed to warm up to room temperature and stirred under nitrogen for 16 hours. EA:water (10 ml; 1:1) was added, the organic layer separated and the aqueous layer washed with EA (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 15-25% EA in hexane to give product as a white solid.

Example 15

Synthesis of Methanone, (pyrrolidinyl)tricyclo[3.3.1.1^{3,7}]dec-1-yl-

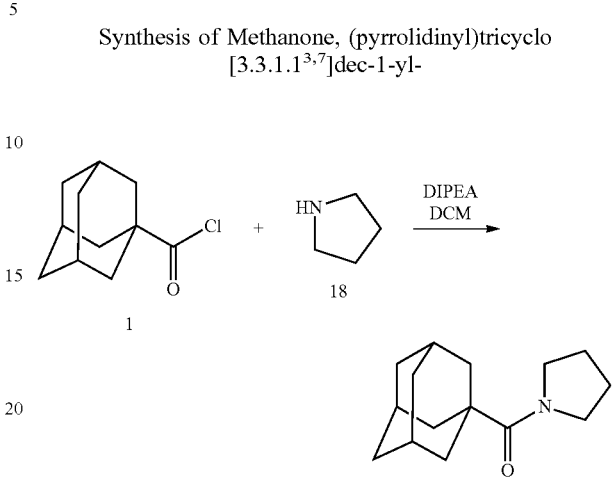

Tricyclo[3.3.1.1^{3,7}]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and pyrrolidine (18) (131 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with 1 N HCl, water and dried under high vacuum. The crude product was purified over a silica gel bed to give product as a white solid (334 mg, 95%).

Example 16

Synthesis of Methanone, (hexahydroazepinyl)tricyclo[3.3.1.1^{3,7}]dec-1-yl- (Compound C5)

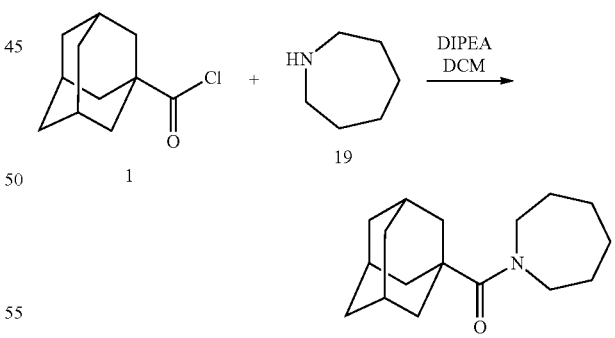

Tricyclo[3.3.1.1^{3,7}]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and azepane (19) 192 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 17

Synthesis of Methanone, (2-methyl-1-piperidinyl) tricyclo[3.3.1.1$^{3,7}$]dec-1-yl- (Compound C12)

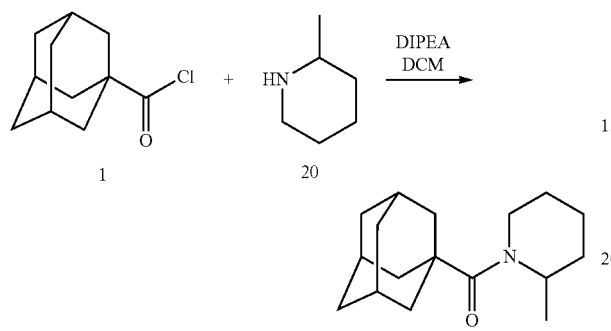

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 2-methylpiperidine (20) (216 mg, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 18

Synthesis of Methanone, (3,5-dimethyl-1-piperidinyl)tricyclo[3.3.1.1$^{3,7}$]dec-1-yl-(Compound C15)

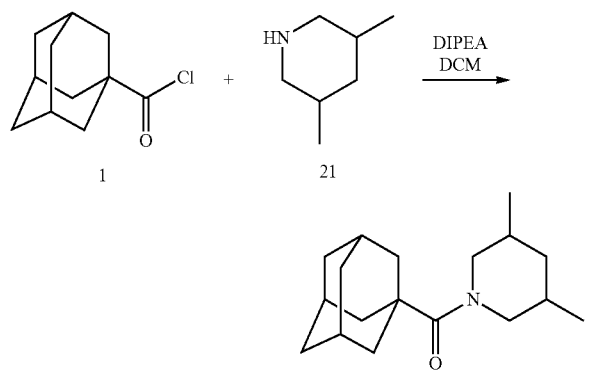

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 3,5-dimethylpiperidine (21) (226 µL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. Water was added, the organic layer separated and the aqueous layer washed with DCM (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 12:88 EA:hexane to give product as a white solid.

Example 19

Synthesis of Methanone, (4-methyl-4-ethy-piperidinyl)tricyclo[3.3.1.1$^{3,7}$]dec-1-yl-(Compound C16)

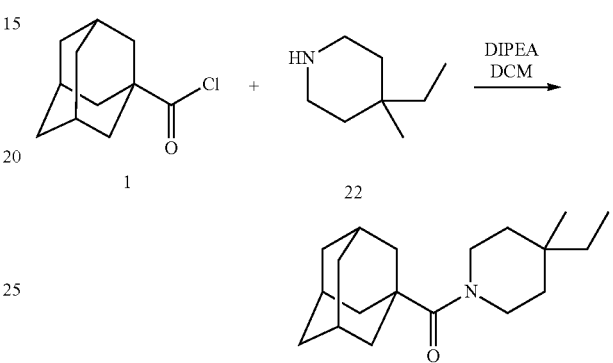

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 4-ethyl-4-methylpiperidine (22) (216 mg, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. Water was added, the organic layer separated and the aqueous layer washed with DCM (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 12:88 EA:hexane to give product as a white solid.

Example 20

Synthesis of Methanone, (3,3-diethyl-pyrrolidinyl) tricyclo[3.3.1.1$^{3,7}$]dec-1-yl- (Compound C17)

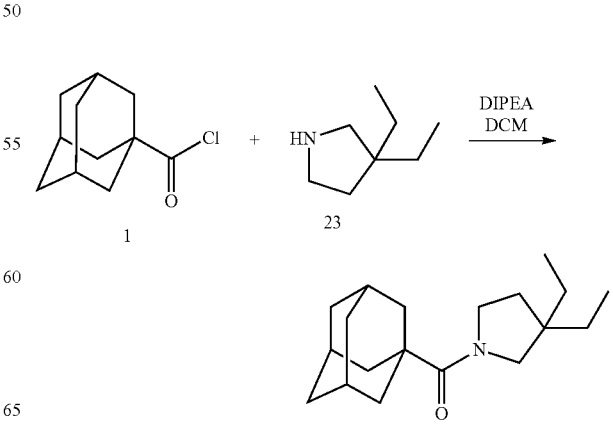

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 3,3-diethylpyrrolidine (23) (216 mg, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 21

Synthesis of Methanone, (cyclobutylaminyl)tricyclo[3.3.1.1$^{3,7}$]dec-1-yl-

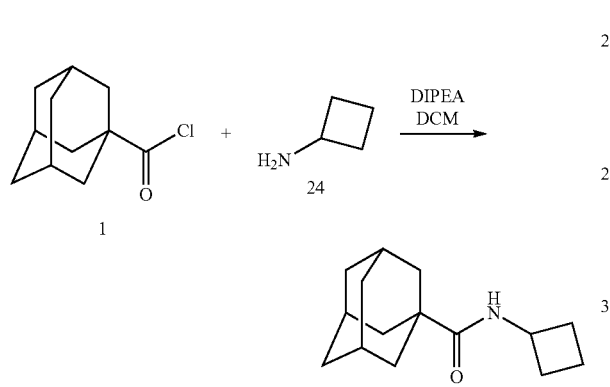

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and cyclobutylamine (24) (150 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with 1 N HCl, water and dried under high vacuum. The crude product was purified over a silica gel bed to give product as a white solid.

Example 22

Synthesis of Methanone, (2,2-dimethylpropylaminyl)tricyclo[3.3.1.1$^{3,7}$]dec-1-yl-(Compound C20)

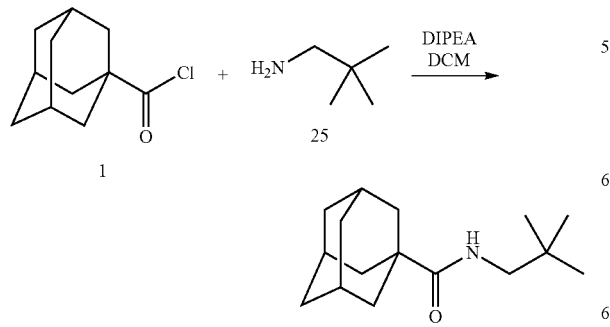

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 2,2-dimethylpropylamine (25) (150 µL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified over a silica gel bed to give product as a white solid.

Example 23

Synthesis of Methanone, (N,N-diisopropyl)tricyclo[3.3.1.1$^{3,7}$]dec-1-yl- (Compound C18)

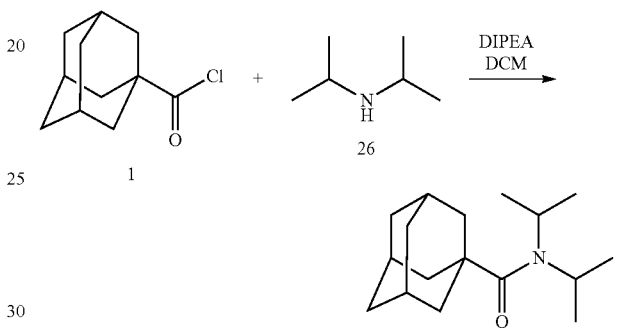

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and diisopropylamine (26) (232 µL, 1.7 mmol) were mixed and added to the Tricyclo[3.3.1.13,7]decane-1-carbonyl chlorides solution slowly. The reaction mixture was allowed to warm up to room temperature and stirred under nitrogen for 16 hours. The obtained precipitate was filtered and washed with EA. The filtrates were combined and sequentially washed with 0.1 N HCl, water, saturated NaHCO$_3$, saturated NaCl, dried (Na$_2$SO$_4$), filtered and the solvents removed to give crude product which was purified by FC on silica gel using 20:80 EA:hexane to give product as a white solid.

Example 24

Synthesis of Methanone, (1,3-dimethyl-butylaminyl)tricyclo[3.3.1.1$^{3,7}$]dec-1-yl-(Compound C22)

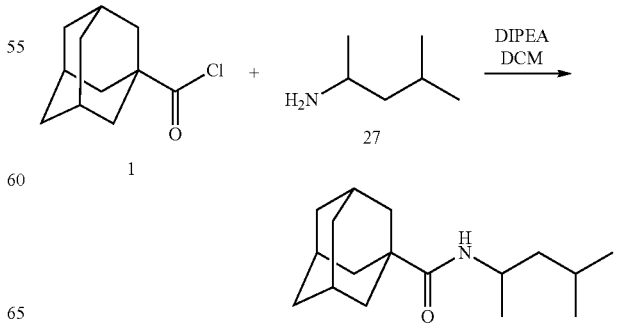

Tricyclo[3.3.1.1$^{3,7}$]decane-1-carbonyl chloride (1) (300 mg, 1.6 mmol) was stirred under nitrogen atmosphere in DCM (4 mL) and the solution cooled to 0° C. in an ice bath. DIPEA (300 μL, 1.7 mmol) and 1,3-dimethylbutylamine (27) (239 μL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified over a silica gel bed to give product as a white solid.

Example 25

Synthesis of Methanone, (Tricyclo[3.3.1.1$^{3,7}$]decanyl)-N-tricyclo[3.3.1.1$^{3,7}$]dec-1-yl-(Compound C8)

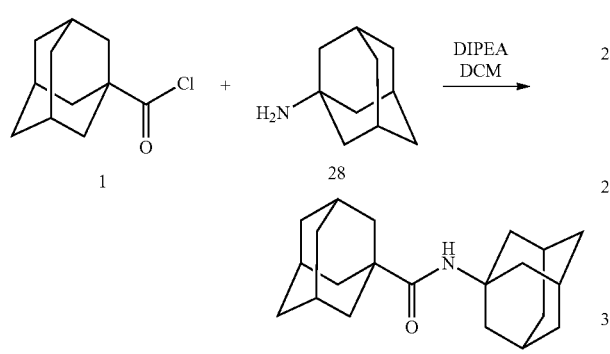

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 μL, 1.7 mmol) and Tricyclo[3.3.1.1$^{3,7}$]decan-1-amine (28) (257 mg, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified by FC on silica gel using 15:85 EA:hexane containing 0.1% DIPEA, followed by elution with CHCl$_3$ to give product as a white solid.

Example 26

Methanone, (3-aminotetrahydrofuranyl)tricyclo [3.3.1.1$^{3,7}$]dec-1-yl-

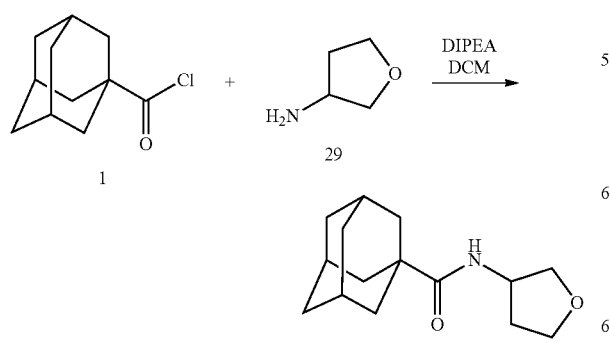

DIPEA (1.93 ml, 11.1 mmol) was added to a solution of Tricyclo[3.3.1.1$^{3,7}$]decane-1-carbonyl chloride (1) (2 g, 10.1 mmol) and 3-aminotetrahydrofuran; (29)(1.0 ml, 11 mmol) in DCM (20 ml) and the solution stirred at room temperature for 4 hours. The solution was washed with 0.1 N HCl (30 ml), saturated NaHCO$_3$ (30 ml), dried (Na$_2$SO$_4$), filtered and the solvents removed to give crude product which was further purified via crystallization from 15% EA in hexanes to give as a white solid.

Example 27

Methanone, (morphonyl)tricyclo[3.3.1.1$^{3,7}$]dec-1-yl-(Compound C1)

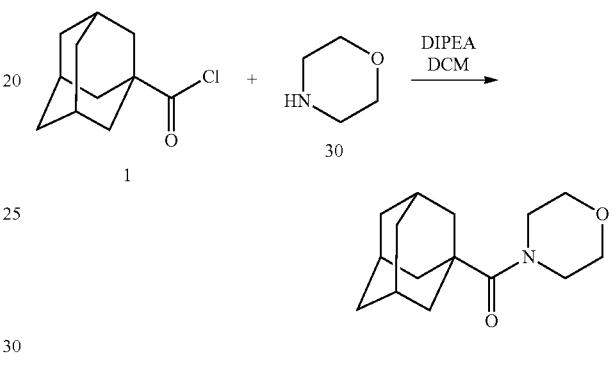

DIPEA (1.93 ml, 11.1 mmol) was added to a solution of Tricyclo[3.3.1.1$^{3,7}$]decane-1-carbonyl chloride (1) (2 g, 10.1 mmol) and morpholine; (30)(1.1 g) in DCM (20 ml) and the solution stirred at room temperature for 4 hours. The solution was washed with 0.1 N HCl (30 ml), saturated NaHCO$_3$ (30 ml), dried (Na$_2$SO$_4$), filtered and the solvents removed to give crude product which was further purified via crystallization from 15% EA in hexanes to give as a white solid.

Example 28

Methanone, (piperidiny)tricyclo[3.3.1.1$^{3,7}$]dec-1-yl-(Compound C2)

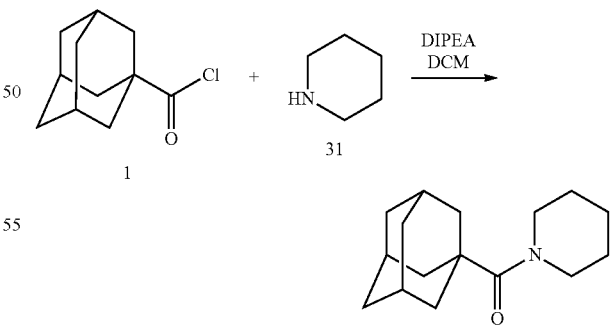

DIPEA (1.93 ml, 11.1 mmol) was added to a solution of Tricyclo[3.3.1.1$^{3,7}$]decane-1-carbonyl chloride (1) (2.1 g, 10.1 mmol) and piperidine (31) (1.1 g) in DCM (20 ml) and the solution stirred at room temperature for 4 hours. At this time, TLC 15:85 EA [ethylacetate: hexane, 20 μL aliquot into MTBE:1 N HCl (400 μL:400 μL)] showed the formation of a single product and some starting material. The solution was washed with 0.1N HCl (30 ml), saturated NaHCO$_3$ (30 ml), dried (Na$_2$SO$_4$), filtered and the solvents removed to give crude product which was further purified via crystallization from 15% EA in hexanes to give as a white solid.

Example 29

Typical personal care photoprotective compositions within the scope of the invention include the following formulations:

Formulation 1

| MATERIAL | % w/w |
|---|---|
| Methylparaben | 0.2 |
| Propylparaben | 0.1 |
| Disodium EDTA | 0.1 |
| Carbopol | 0.4 |
| Glycerin | 2.5 |
| Xantham Gum | 0.5 |
| Niacinamide | 0.1 |
| Potassium Hydroxide (50%) | 0.9 |
| Phenylbenzimidazole Sulfonic Acid (Ensulizole) | 1.5 |
| Sodium Hydroxide (40%) | 0.5 |
| Stearic Acid | 2.4 |
| Glycol Stearate/Stearamide AMP | 1.4 |
| Glyceryl Monostearate | 0.6 |
| PEG-100 Stearate | 1.2 |
| Butyl Methoxydibenzoylmethane (Parsol 1789) | 3.0 |
| EthylHexyl Salicylate | 5.0 |
| Dimethicone | 1 |
| Phenoxyethanol | 0.7 |
| Tricyclodecane amide - Compound C21 | 2.0 |
| Perfume | 0.3 |
| DI Water | q.s. |

Formulation 2

| MATERIAL | % w/w |
|---|---|
| Methylparaben | 0.2 |
| Propylparaben | 0.1 |
| Disodium EDTA | 0.1 |
| Carbopol | 0.4 |
| Glycerin | 2.5 |
| Xantham Gum | 0.5 |
| Niacinamide | 0.1 |
| Potassium Hydroxide (50%) | 0.9 |
| Phenylbenzimidazole Sulfonic Acid (Ensulizole) | 1.5 |
| Sodium Hydroxide (40%) | 0.5 |
| Stearic Acid | 2.4 |
| Glycol Stearate/Stearamide AMP | 1.4 |
| Glyceryl Monostearate | 0.6 |
| PEG-100 Stearate | 1.2 |
| Butyl Methoxydibenzoylmethane (Parsol 1789) | 3.0 |
| EthylHexyl Salicylate | 5.0 |
| Dimethicone | 1 |
| Phenoxyethanol | 0.7 |
| Tricyclodecane amide - Compound C10 | 2.0 |
| Perfume | 0.3 |
| DI Water | q.s. |

Formulation 3

| MATERIAL | % w/w |
|---|---|
| Methylparaben | 0.2 |
| Propylparaben | 0.1 |
| Disodium EDTA | 0.1 |
| Carbopol | 0.4 |
| Glycerin | 2.5 |
| Xantham Gum | 0.5 |
| Niacinamide | 0.1 |
| Potassium Hydroxide (50%) | 0.9 |
| Phenylbenzimidazole Sulfonic Acid (Ensulizole) | 1.5 |
| Sodium Hydroxide (40%) | 0.5 |
| Stearic Acid | 2.4 |
| Glycol Stearate/Stearamide AMP | 1.4 |
| Glyceryl Monostearate | 0.6 |
| PEG-100 Stearate | 1.2 |
| Butyl Methoxydibenzoylmethane (Parsol 1789) | 3.0 |
| EthylHexyl Salicylate | 5.0 |
| Dimethicone | 1 |
| Phenoxyethanol | 0.7 |
| Tricyclodecane amide - Compound C14 | 2.0 |
| Perfume | 0.3 |
| DI Water | 75.7 |

Example 30

Sebum suppression effect of the tricyclodecane amides suitable for use in the present invention was investigated.

Sebocyte Assay Procedure:

Secondary cultures of human sebocytes obtained from an adult male were grown in 96-well tissue culture plates (Packard) until three days post-confluence. Sebocyte growth medium consisted of Clonetics Keratinocyte Basal Medium (KBM) supplemented with 14 µg/ml bovine pituitary extract, 0.4 µg/ml hydrocortisone, 5 µg/ml insulin, 10 ng/ml epidermal growth factor, 1.2×10$^{-10}$ M cholera toxin, 100 units/ml penicillin, and 100 µg/ml streptomycin. All cultures were incubated at 37° C. in the presence of 5% CO$_2$. Medium was changed three times per week.

On the day of experimentation, the growth medium was removed and the sebocytes washed three times with sterile Dulbecco's Modified Eagle Medium (DMEM; phenol red free). Fresh DMEM was added to each sample (triplicates) with 5-microliters of test agent solubilized in ethanol. Controls consisted of addition ethanol alone. Each plate was returned to the incubator for 20-hours followed by the addition of $^{14}$C-acetate buffer (5 mM final concentration, 56 mCi/mmol specific activity). Sebocytes were returned to the incubator for 4-hours after which each culture was rinsed 3-times with phosphate buffered saline to remove unbound label. Radioactive label remaining in the sebocytes was determined using a Packard Microbeta, scintillation counter. The results that were obtained are summarized in Table 1. Phenol Red, a known sebum suppressive agent, was employed as a positive control.

TABLE 1

| Compound Number | % Reduction at 10 microMolar | % Reduction at 100 microMolar |
|---|---|---|
| C11 | 39.3 | 76.6 |
| C15 | 40.1 | 71 |
| C16 | 49.8 | 80.7 |
| C10 | 63.4 | 89.6 |
| C9 | 81.2 | 86.8 |
| C13 | 63.5 | 90.4 |
| C14 | 52.8 | 76 |
| C8 | 19.1 | 58.8 |
| C20 | 49.5 | 82.8 |
| C4 | 16.3 | 27.9 |
| C17 | 32.2 | 65.2 |
| C12 | 24.5 | 51 |
| C18 | 42.0 | 52.5 |
| C21 | 26.4 | 43.5 |

TABLE 1-continued

| Compound Number | % Reduction at 10 microMolar | % Reduction at 100 microMolar |
|---|---|---|
| C5 | 32.4 | 50.5 |
| C19 | 35.9 | 54.,7 |
| C22 | 29.1 | 45.3 |
| C2 | 34.3 | 51.6 |
| C1 | 35.4 | 78.5 |
| C7 | 58.9 | 73.4 |
| C6 | 24.8 | 39.4 |
| Phenol Red (Positive Control) | 17.1 | 65.1 |

Example 31

SPF, UV-A, and UV-B improvement of compositions within the scope of the invention was investigated.

Control Formulation - Vanishing cream (Stearic acid) base

| MATERIAL | % w/w |
|---|---|
| Stearic Acid | 17 |
| Cetyl Alcohol | 0.53 |
| Methyl Paraben | 0.2 |
| Glycerin | 1.0 |
| Potassium Hydroxide (KOH, 50%) | 0.96 |
| Disodium EDTA | 0.04 |
| Dimethicone | 0.5 |
| Propyl Paraben | 0.1 |
| Isopropyl Myristate | 0.75 |
| Octyl Methoxy Cinnamate (Parsol MCX) | 3.0 |
| t-butylmethoxydibenzoylmethane (Parsol 1789) | 1.5 |
| Niacinamide | 1.25 |
| Phenoxyethanol | 0.4 |
| DI Water | q.s |

In Vitro SPF Evaluation

In vitro SPF measurement was done using the Optometric 290S SPF meter. The product was applied at a dosage of 2 mg/cm$^2$ on PMMA (polymethylmethacrylate) plate (7 cm×7 cm) and allowed to air dry for 30 minutes. The average SPF value was obtained from 6 SPF readings per plate. Two duplicated runs, the standard deviation from the average was ±2 SPF units. % increase of in vitro SPF versus control calculation: (measured SPF for selected formulation−measured SPF of control)/measured SPF of control×100. The results that were obtained are summarized in Table 2.

TABLE 2

| Formulation | In vitro SPF (2 mg/cm2) | % Increase over control |
|---|---|---|
| Control | 16 | |
| Control + 2% Compound C10 | 22 | 37.5 |
| Control + 2% Compound C21 | 23 | 44 |
| Control + 2% Compound C14 | 24 | 50 |
| Control + 2% Octadecanamide | 17 | 6 |

In Vitro MPF Evaluation

MPF=monochromatic protection factor=1/Transmittance at a specific wavelength (lower transmittance gives higher MPF therefore higher absorption for the sunscreen). 305 nm=UVB, 360 nm=UVA. MPF was measured using the same apparatus as SPF above. MPF % increase over control (measured MPF at 305 nm and 360 nm for selected formulation−measured MPF at 305 nm and 360 nm of control)/measured MPF at 305 nm and 360 nm of control×100.

The results that were obtained are summarized in Table 4.

TABLE 3

| Formulation from US20110104087 A1* | MPF % increase over control | |
|---|---|---|
| | 305 nm | 360 nm |
| Control | | |
| 2 | 5.2 | 87.9 |
| 3 | 23.8 | 132 |
| 4 | 12 | 164 |
| 5 | 13.1 | 132 |
| 6 | −2 | 126 |

*Calculated % increase based on MPF values in Table III of US20110104087 A1.

TABLE 4

| Formulation | MPF % increase over control | |
|---|---|---|
| | 305 nm | 360 nm |
| Control + 2% Compound C10 | 38.2 | 45.8 |
| Control + 2% Compound C21 | 52.5 | 62.5 |
| Control + 2% Compound C14 | 65.7 | 75 |
| Control + 2% Octadecanamide | 2.8 | −4.2 |

It can be seen from Tables 2 and 4 that compositions within the scope of the invention increased both UV-A and UV-B (Table 4) as well as SPF protection (Table 2). Linear amides with similar chain length (octadecanamide) did not achieve these improvements (see the last row in each of Table 2 and Table 4). Similarly, other amides reported in US '087 did not achieve both UV-A and UV-B improvement (Table 3).

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

The invention claimed is:

1. A personal care photoprotection composition comprising:
   a) from about 1 to about 20%, by weight of the composition, of an organic UV-B sunscreen;
   b) from about 1 to about 10%, by weight of the composition of an organic UV-A sunscreen;
   c) from about 0.0001% to about 20% of a tricyclodecane amide; and
   d) a cosmetically acceptable carrier,
   wherein the tricyclodecane amide is selected from:

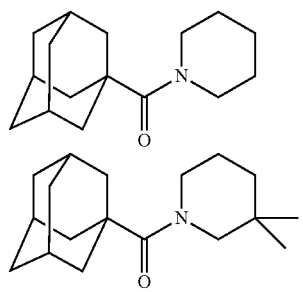

-continued

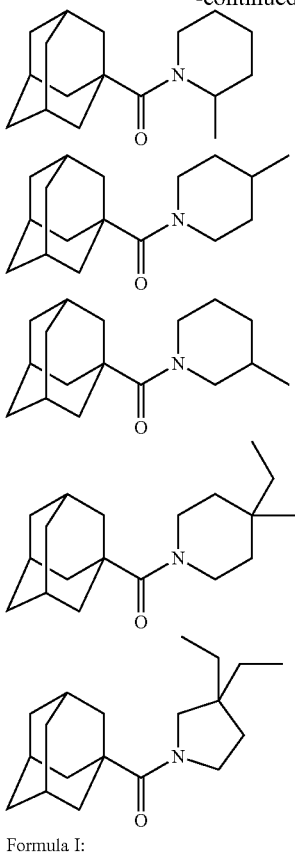

and

Formula I:

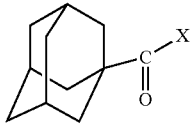

where X is selected from:

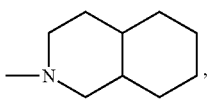

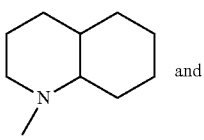
and

-continued

Formula II:

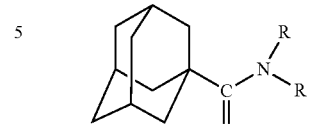

wherein each R is independently hydrogen, or $C_3$ to $C_{10}$, linear or branched alkyl, with the proviso that both R groups are not simultaneously hydrogen.

2. The composition of claim 1 wherein the composition is water and oil emulsion.

3. The composition of claim 1 further comprising an inorganic sunscreen.

4. The composition of claim 1 further comprising fatty acid and fatty acid soap.

5. The composition of claim 1 further comprising a skin lightening compound.

6. The composition of claim 1 further comprising a surfactant.

7. A method of improving UV-A, UV-B and SPF protection, the method comprising applying to the human body the composition of claim 1.

8. A method of decreasing sebum production in the skin, the method comprising applying to the skin the composition of claim 1.

9. The composition of claim 5 wherein the skin lightening compound is selected from the group consisting of placental extract, lactic acid, niacinamide, arbutin, kojic acid, ferulic acid, hydroquinone, resorcinol and derivatives including 4-substituted resorcinols, 12-hydroxystearic acid and mixtures thereof.

10. The composition of claim 1 further comprising a retinoid.

11. The composition of claim 10 wherein the retinoid is retinol propionate.

12. The composition of claim 1 further comprising a preservative.

13. The composition of claim 12 wherein the preservative is selected from the group consisting of iodopropynyl butyl carbamate, phenoxyethanol, caprylyl glycol, C1-6 parabens, imidazolidinyl urea, sodium dehydroacetate and benzyl alcohol.

14. The composition of claim 1 further comprising octocrylene and caprilyl glycol.

* * * * *